US007682331B2

(12) United States Patent  
Carrez et al.

(10) Patent No.: US 7,682,331 B2  
(45) Date of Patent: Mar. 23, 2010

(54) DEVICE FOR INTRODUCING A CATHETER WITH A SECURITY NON-PIERCING CAGE PROVIDED WITH A FLEXIBLE BLADE

(75) Inventors: Jean-Luc Carrez, Ecouen (FR); Valéry Dalle, Gouvieux (FR); Pierrick Guyomarc'h, Ermont (FR); Jean-Max Huet, Clichy (FR)

(73) Assignee: Vygon, Ecouen (FR)

( * ) Notice: Subject to any disclaimer, the term of this patent is extended or adjusted under 35 U.S.C. 154(b) by 91 days.

(21) Appl. No.: 10/598,440

(22) PCT Filed: Feb. 14, 2005

(86) PCT No.: PCT/FR2005/000343

§ 371 (c)(1),  
(2), (4) Date: Oct. 16, 2006

(87) PCT Pub. No.: WO2005/094939

PCT Pub. Date: Oct. 13, 2005

(65) Prior Publication Data

US 2007/0191774 A1 Aug. 16, 2007

(30) Foreign Application Priority Data

Mar. 2, 2004 (FR) .................................. 04 02126

(51) Int. Cl.  
*A61N 1/30* (2006.01)  
*A61M 5/178* (2006.01)

(52) U.S. Cl. .................................... 604/19; 604/164.01  
(58) Field of Classification Search .................... 604/19  
See application file for complete search history.

(56) References Cited

U.S. PATENT DOCUMENTS

| 5,215,528 | A  | * | 6/1993  | Purdy et al. | ............ | 604/164.08 |
| 7,291,128 | B2 | * | 11/2007 | Rossi et al. | ................. | 604/110 |
| 2003/0195471 | A1 | * | 10/2003 | Woehr et al. | ........... | 604/164.08 |

* cited by examiner

*Primary Examiner*—Nicholas D Lucchesi  
*Assistant Examiner*—Jason Flick  
(74) *Attorney, Agent, or Firm*—Levine & Mandelbaum

(57) ABSTRACT

A device for introducing a catheter into a body site through the skin by means of an security non-piercing cage includes a steel spring flexible blade which is disposed in the cross section of the chamber of the nonpiercing cage near the proximal input thereof perpendicularly to a needle and is penetrable by the needle. The blade and the needle are adapted to interact in such a way that the blade is in a resting position and freely transversable by the needle when the needle is pushed in a distal direction, and the blade stops the needle and is flexed thereby when the needle is pulled in a proximal direction beyond a determined axial position in such a way that the flexed blade tilts the needle and exposes the inclined needle to a restoring force which pushes the needle off in the distal direction until the puncture end is stopped against the chamber wall. The invention can be used for intravenous catheters.

10 Claims, 8 Drawing Sheets

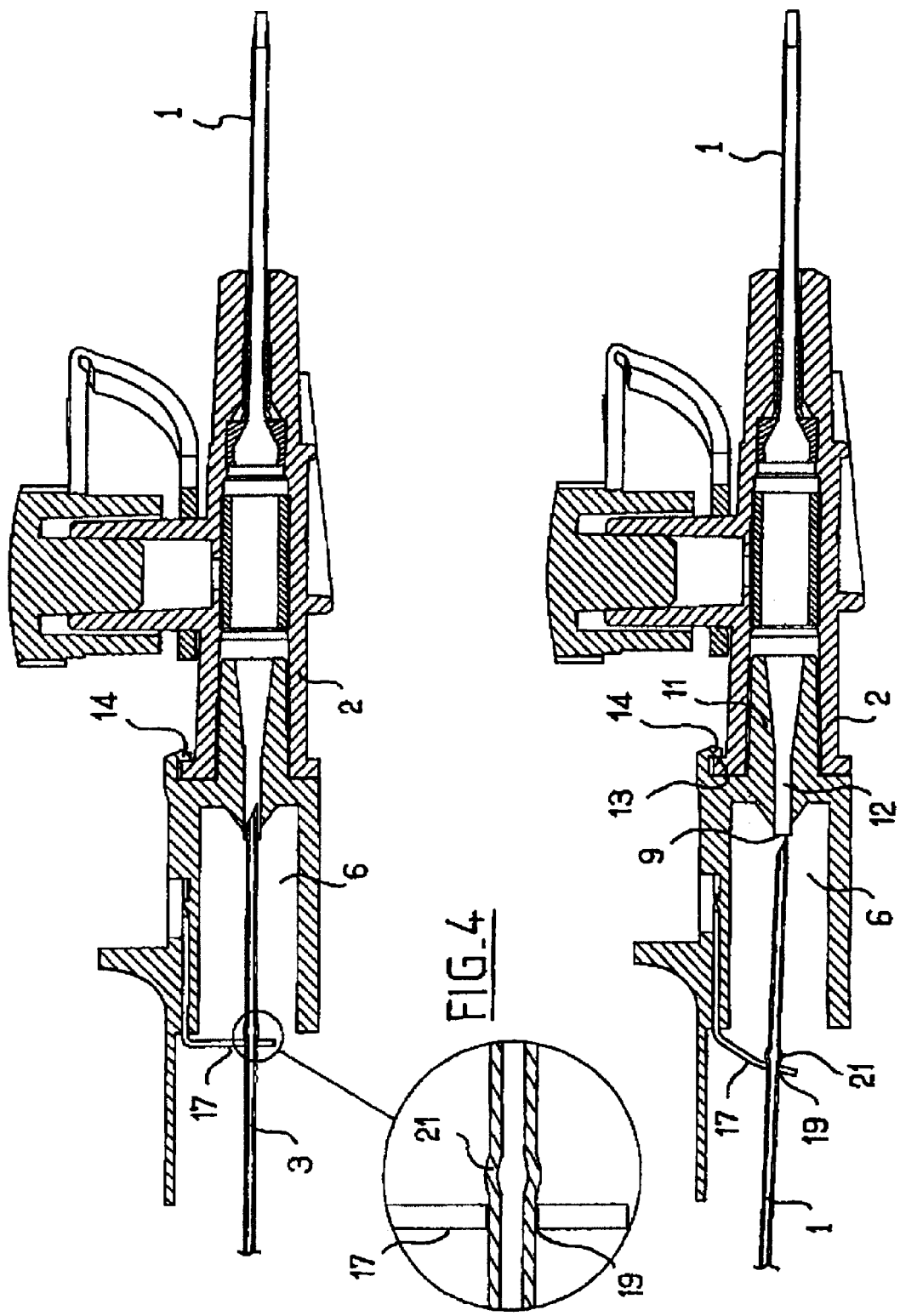

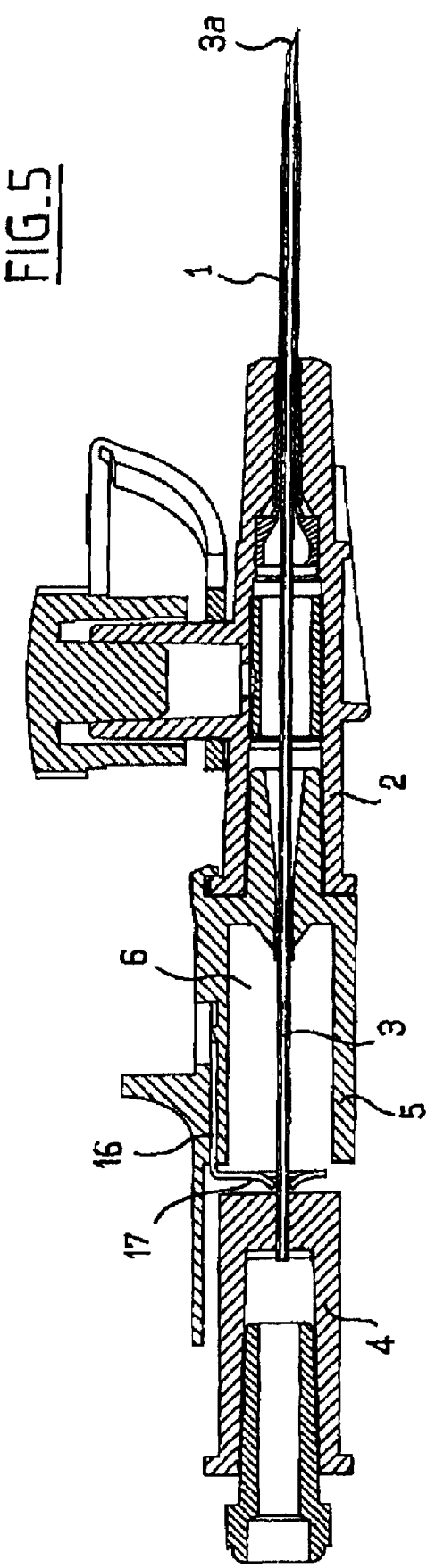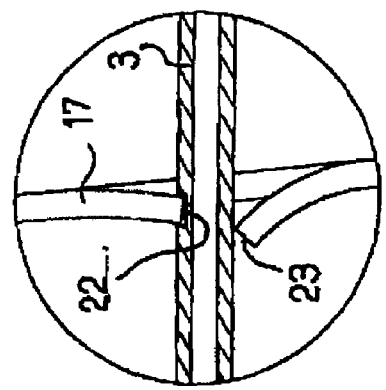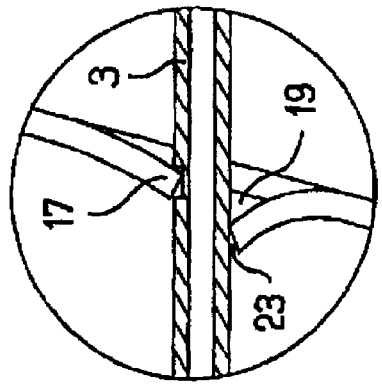

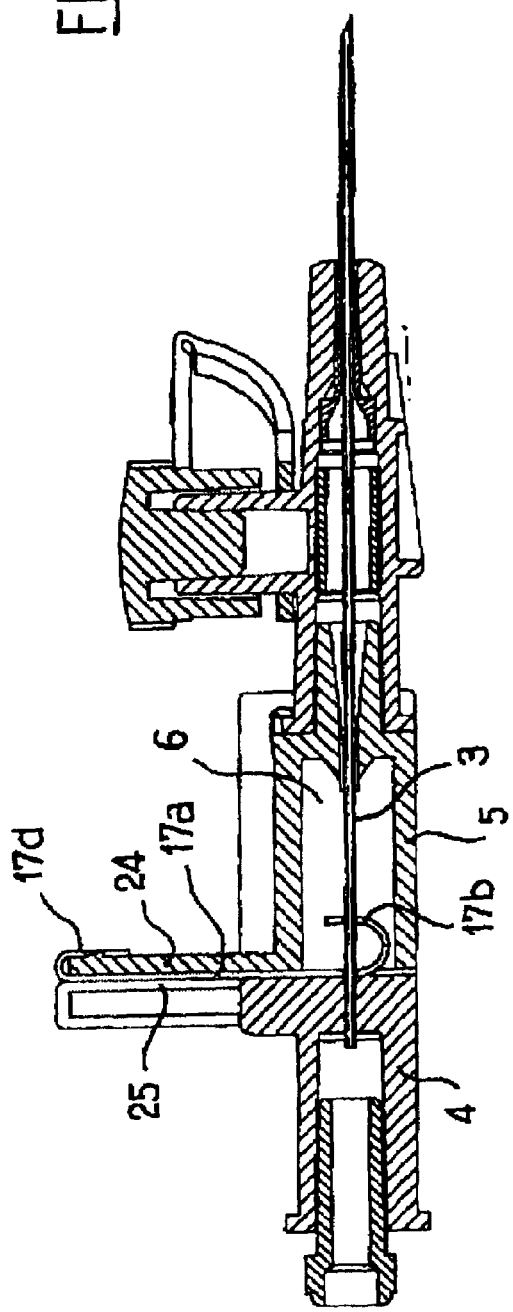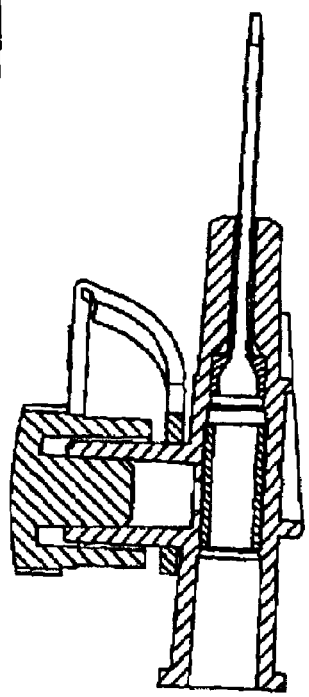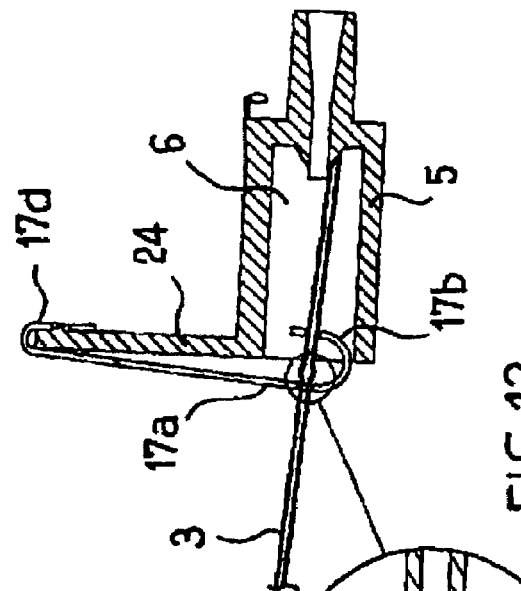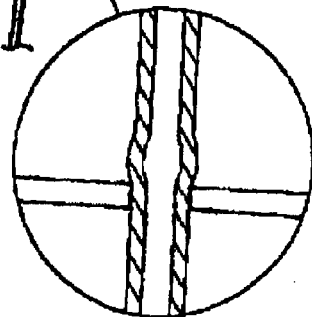

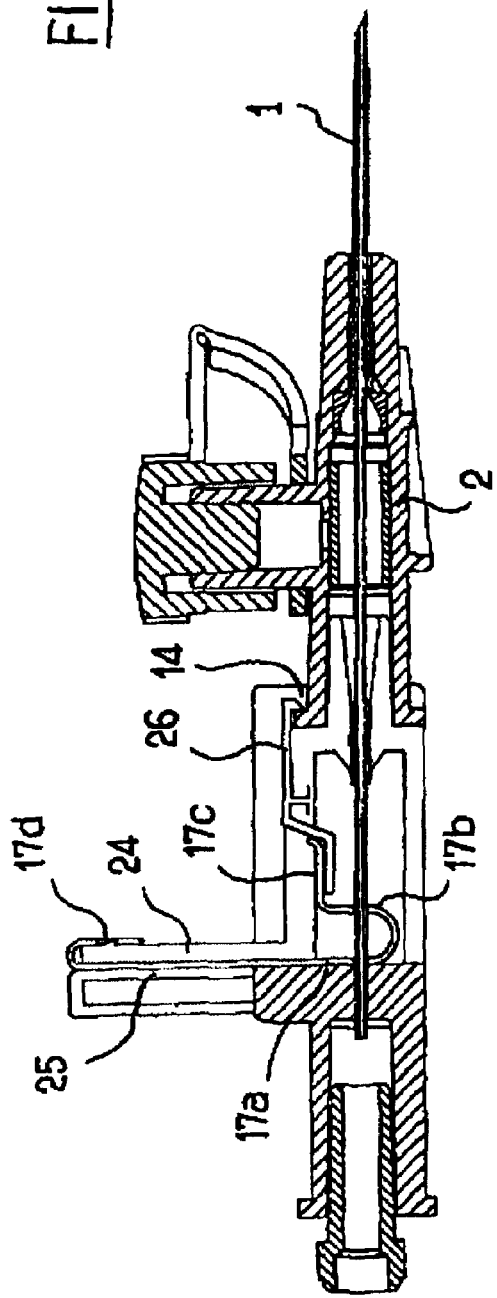
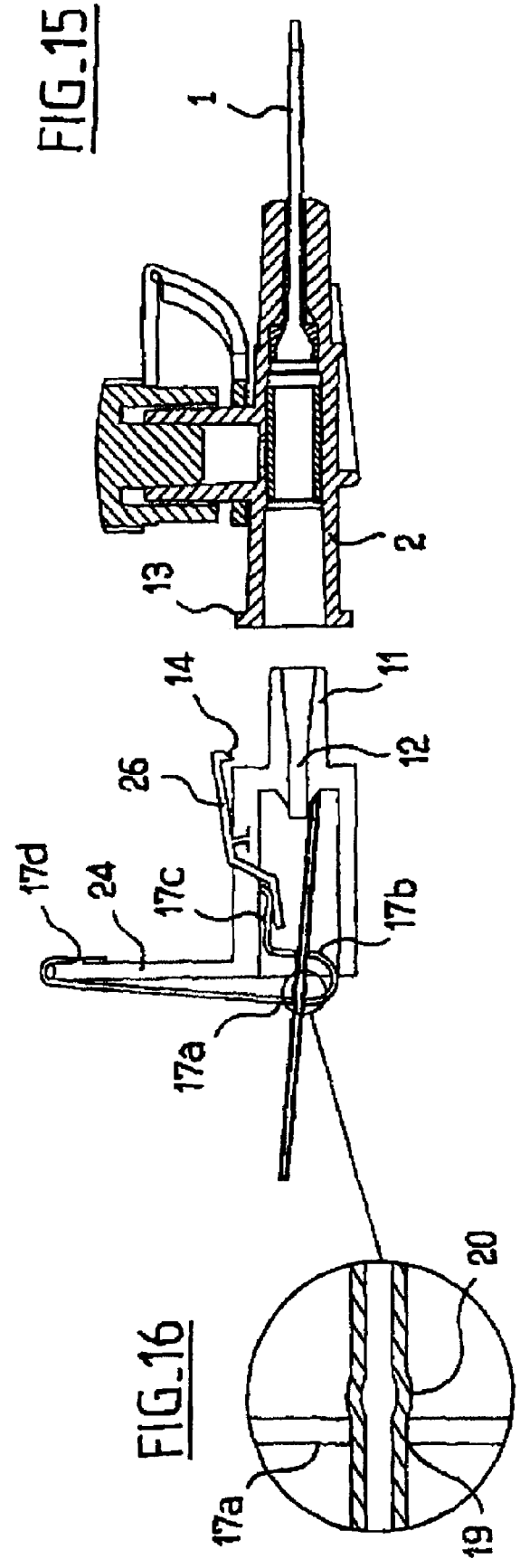

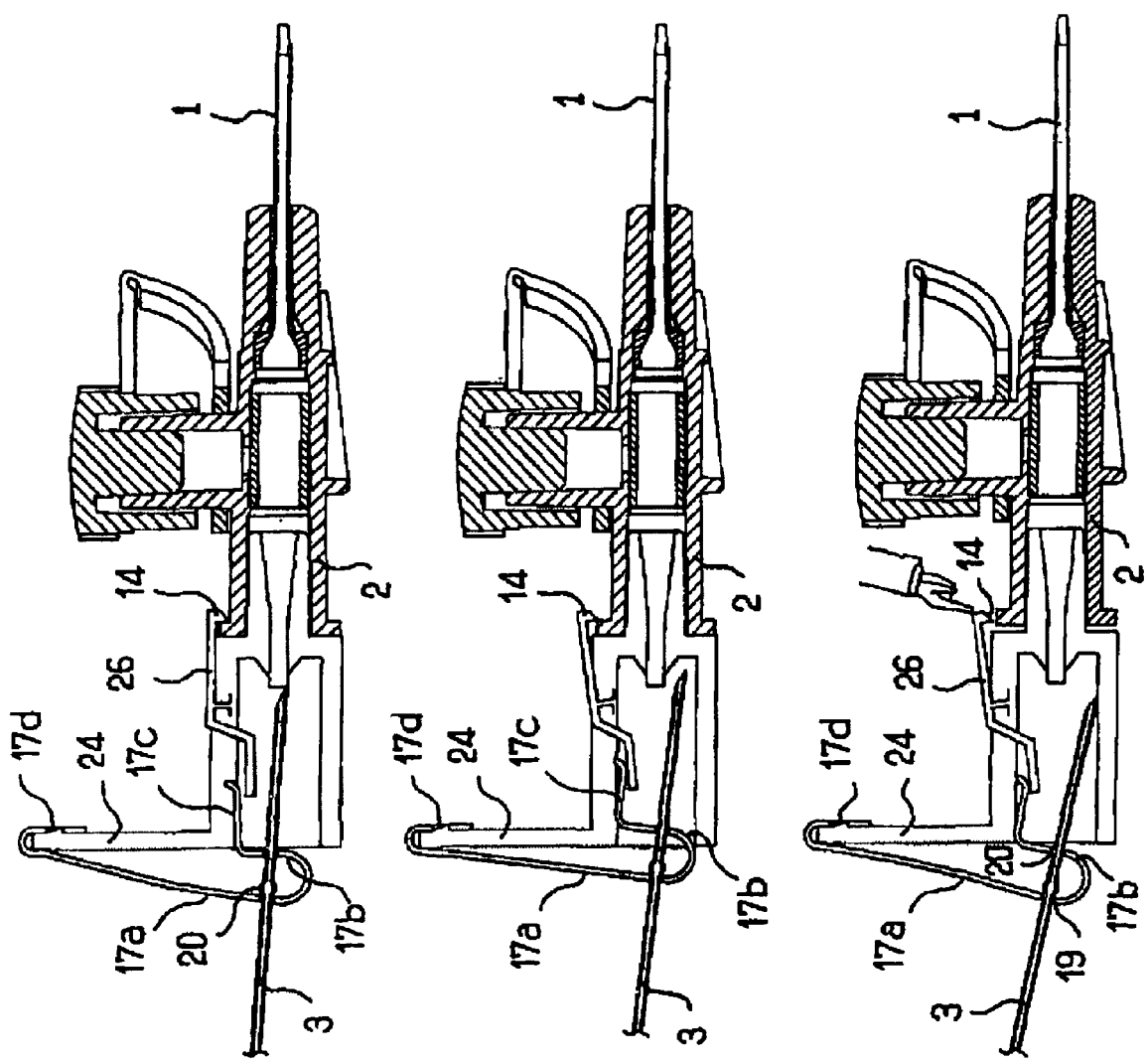

DEVICE FOR INTRODUCING A CATHETER WITH A SECURITY NON-PIERCING CAGE PROVIDED WITH A FLEXIBLE BLADE

BACKGROUND OF THE INVENTION

The invention aims to eliminate the risks of accidental pricking on removal of a puncture needle employed for the insertion of a catheter into any part of the body through the skin.

A large number of such prick-prevention arrangements have been proposes for this purpose.

Publication FR 2 836 385 describes an arrangement in which whole needle with its base is trapped within a case after its removal.

Publications EP 0 554 841 and U.S. Pat. No. 5,322,517 describe safety resources which include a cage to trap the point of the needle after its removal, where this cage contains a sprung steel blade which has a branch traversed by the needle, and another branch which is pre-stressed by the needle in an inactive position in which it bears laterally against the needle and which, in its active position, moves in front of the needle when this contact is removed due to withdrawal of the needle.

Publication EP 0 753 317 describes a cage which slides on the needle and which includes a sprung steel blade pre-stressed by contact with the needle in an inactive position for as long as the needle traverses the cage, and which is freed and acts to divert the needle when the latter has entered into in the cage.

Publication U.S. Pat. No. 5 447 501 describes an arrangement which includes a spring which is pre-stressed by the needle in an inactive position, and which diverts the needle when it is freed by withdrawal of the needle.

Other cage arrangements are also described in publications EP 0 456 694 (or U.S. Pat. No. 5,322,517), U.S. Pat. Nos. 623 499, 5,176,655, and EP 0 891 198 (or U.S. Pat. No. 6,001, 080).

SUMMARY OF THE INVENTION

One objective of this present invention is to provide a simple cage and flexible blade arrangement, operating automatically, and in which the blade is not prestressed by the needle.

The invention concerns and arrangement for the insertion of a catheter into any part of the body, in particular a vein, through the skin, this catheter being equipped with a proximal base, where this arrangement includes a needle with a puncture end and also includes an anti-prick cage which extends the catheter base in the proximal direction, where this chamber forms a chamber through which the needle slides from a proximal entrance to a distal exit, and is equipped with sprung flexible steel blade to hold the puncture end of the needle in the chamber when the needle is withdrawn from the cannula, this blade being positioned across the chamber close to the proximal entrance of the chamber perpendicular to the needle and traversed by the needle, with the blade and the needle including resources that combine so that the blade is at rest and traversed freely by the needle when the needle is pushed in the distal direction and so that the blade stops the needle, and is bent by the needle, when the needle is drawn in the proximal direction beyond a given axial position, so that the bent blade inclines the needle, and applies a return force to the needle which tends to force the needle back in the distal direction until the puncture end of the inclined needle comes up against a wall of the chamber.

In a preferred implementation, the flexible blade has a perforation for the passage of the needle, and the needle has a section of the needle modified locally so that it can be stopped by the perforation in the blade during the withdrawal movement of the needle, this modified section being located at a distance from the puncture end of the needle so that the contact of the modified section with the perforation in the blade occurs after this end has entered into the chamber during the withdrawal movement of the needle.

In preferred methods of implementation, the invention also has one or more of the following characteristics:
- the chamber has an end wall in the distal direction which forms a groove in which the puncture end of the inclined needle lodges;
- ahead of the chamber, the cage has a nose which fits, without locking, into the catheter base, and which is traversed longitudinally by an aperture for the passage of the needle;
- the catheter base has an external rim, and the cage includes a device which has a dog which locks onto this rim for temporary attachment of the cage to the base;
- the dog comprises the end of a lever, and the flexible blade is shaped to operate by contact with this lever so as to free the dog from the rim of the catheter base when the blade has been sufficiently deflected.

DESCRIPTION OF THE DRAWINGS

The following description is of various implementations of an arrangement according to the invention for the insertion of a short catheter into a vein, with reference to the appended drawings in which:

FIG. 2 shows the implementation of FIG. 1 during 30 two successive stages of the operation to withdraw the needle;

FIG. 4 is a magnified view of a detail of the assembly of FIG. 2;

FIG. 5 shows, in longitudinal section, an implementation variant of the assembly of FIG. 1, ready for use, with the flexible blade shown at rest;

FIG. 7 is a magnified view of a detail of the assembly of FIG. 6;

FIG. 8 is a magnified view of the same detail, during a later stage of the withdrawal;

FIG. 9 shows, in longitudinal section, another implementation of an assembly according to the invention, ready for use, with the flexible blade shown at rest;

FIG. 11 shows the assembly of FIG. 9 after 30 separation of the cage and the cannula;

FIG. 12 is a magnified view of a detail of the assembly of FIG. 9;

FIG. 13 shows, in longitudinal section, another implementation of an assembly according to the invention, ready for use, with the flexible blade shown at rest;

FIG. 14 shows the implementation of FIG. 13 during successive stages of the operation to withdraw the needle;

FIG. 15 shows the implementation of FIG. 13 after separation of the cage and the cannula, and FIG. 16 is a magnified view of a detail of the assembly of FIG. 12.

DESCRIPTION OF THE PREFERRED EMBODIMENT

Figure 1:
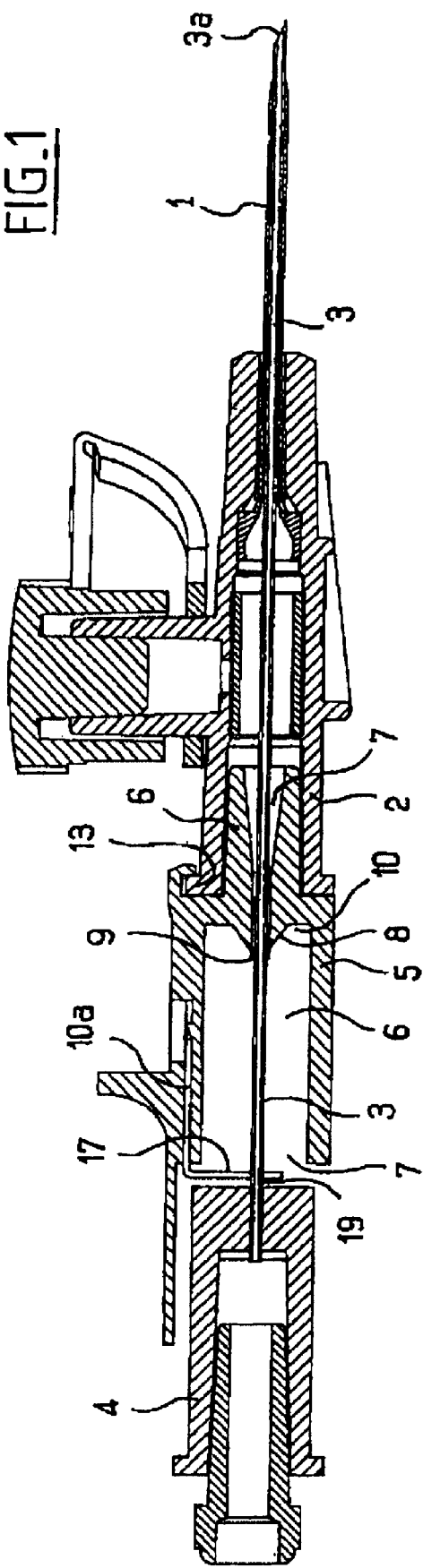
FIG. 1 shows, in longitudinal section, a first implementation, ready for use, with the flexible blade shown at rest.

The figures show a cannula composed of a short tubular catheter (1) equipped with a proximal base (2), a needle (3) which has a puncture end (3a) and which is equipped with a proximal base (4), and an anti-prick cage.

The cage (5) forms a chamber (6) which has a proximal needle entrance (7) oriented toward the base of the needle, and an opposite end wall (8) which has a distal needle exit (9) oriented toward the catheter base.

Preferably, the end wall of the chamber forms a groove 20 around the exit from the chamber (10).

Ahead of the chamber, the cage includes a nose (11) which fits, without locking, into the catheter base, and which is traversed longitudinally by an aperture (12) for the passage of the needle.

The catheter base has an external rim (13), composed of one of the threads on the base for example, when the latter is threaded on the outside, and the cage includes a mobile dog (14) which locks onto this to hold the cage onto the base in a removable manner.

In the implementations of FIGS. 1 and 5, the cage includes a sprung steel blade shaped as an L, which has a longitudinal branch (16) fixed to a longitudinal wall of the chamber, and a flexible transverse branch (17) located close to the proximal entrance (7) of the chamber and equipped with a perforation (19) lined up with the exit (9) of the chamber when this flexible branch is at rest (FIGS. 1 and 5) for the passage of the needle.

In a manner which is known of itself, the needle has a local change of section chosen so as not to compromise the sliding of the needle in the cannula while also being large enough to be stopped by the perforation (19) in the flexible branch of the blade which is located at the entrance of the chamber In the implementations of FIGS. 9 and 13, the flexible branch (17) is shaped as a U, constituting a rear transverse branch (17a) located to the entrance of the chamber and equipped with a perforation (19) for the passage of the needle, and a front transverse branch (17b) parallel to the first branch, located in the said chamber and equipped with a perforation (20) for the passage of the needle and sufficiently wide to also allow passage of the said modified section of the needle, while the perforation (19) stops this modified section. The perforations (19 and 20) are aligned with each other and aligned with the exit of the chamber when the flexible branch is at rest.

By way of guidance, and in no way limiting, two examples of such a modification have been shown which are known in themselves, namely respectively, a modification in the form of a local bulge (21) in the wall of the needle (FIG. 4) and a modification composed of a slot (22) in this wall (FIGS. 7 and 8). In the first case, the perforation (19) in the flexible blade can be merely cylindrical, while in the second case, the blade has claws (23) at the position of the perforation which are designed to bite into the wall of the needle.

In the first case, it can be seen that the needle will not be blocked in the blade and will still be able to slide in the distal direction (toward the front) while in the second case the needle will be blocked.

In all cases, the modification will be effected after threading of the needle.

This U-shaped blade guides the needle at two points and obliges it to assume the orientation imposed by the deviation of the blade.

In the implementations of FIGS. 9 and 13, the cage includes a transverse plate (24) projecting laterally and against which presses one wall (25) of the base (4) of the needle when the needle is in its working position.

In the implementations of FIGS. 9 and 13, the flexible blade (17b) is suspended by a branch (17d) turned onto the transverse plate (24) of the cage.

In the implementation of FIG. 13, in order to allow the separation of the cage from the catheter base, the dog (14) used for the temporary attachment of the cage to the base constitutes the end of a lever (26), and the flexible blade is shaped to operate by contact with this lever so as to free the dog from the rim of the catheter base when the blade has bent sufficiently. In the case presented as an example only, the flexible blade includes, for this purpose, a third branch (17c), which continues the second branch more or less at right angles to this branch, and which presses onto this lever to operate it when the blade bends.

The arrangement of FIG. 1 is applied as follows:

After effecting the vein penetration with the arrangement as shown in FIG. 1, the catheter is pushed toward the front into the vein while holding the needle, with the cage remaining attached to the catheter base and moving away from the base of the needle.

When the catheter is in place, the needle is drawn backwards while holding the catheter (FIG. 2), until the bulge of the needle makes contact with the hole of the blade which it cannot cross.

Figure 3:
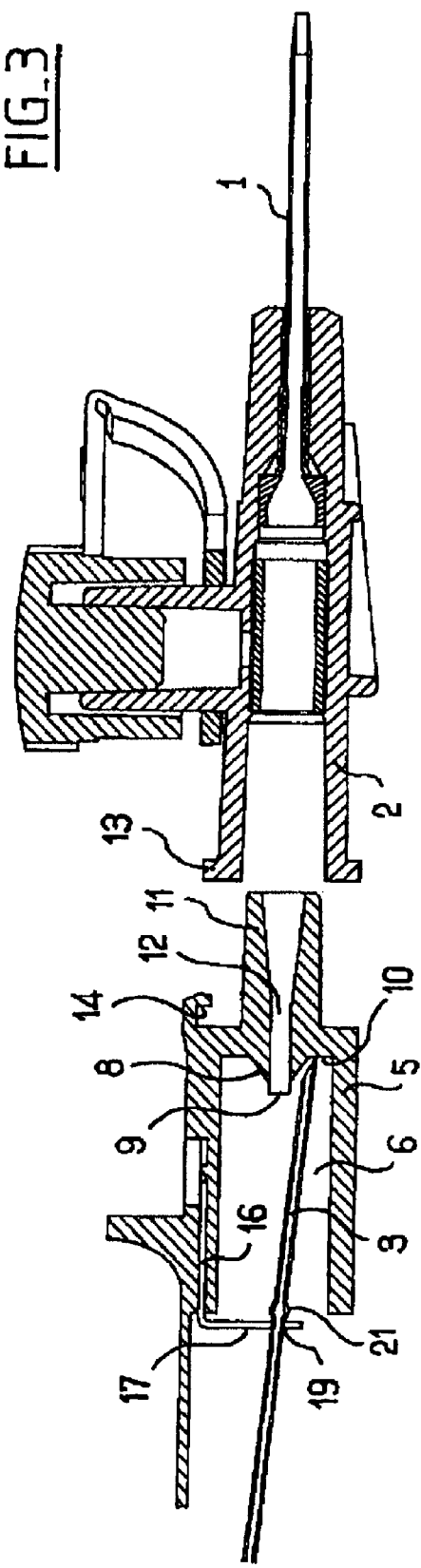
FIG. 3 shows the assembly of FIG. 1 after separation of the cage and the cannula.
Figure 6:
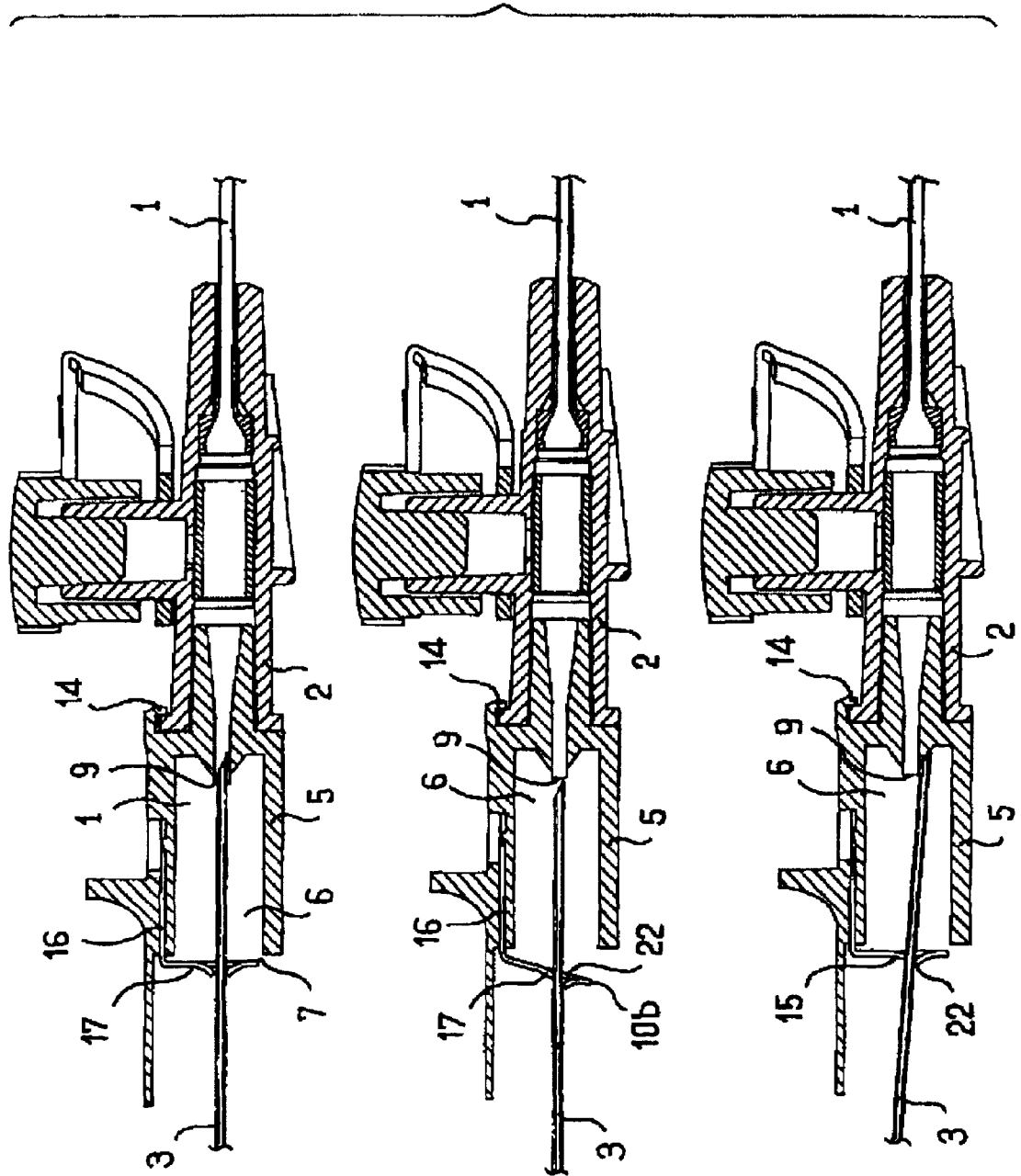
FIG. 6 shows the implementation of FIG. 5 during successive stages of the operation to withdraw the needle.
Figure 10:
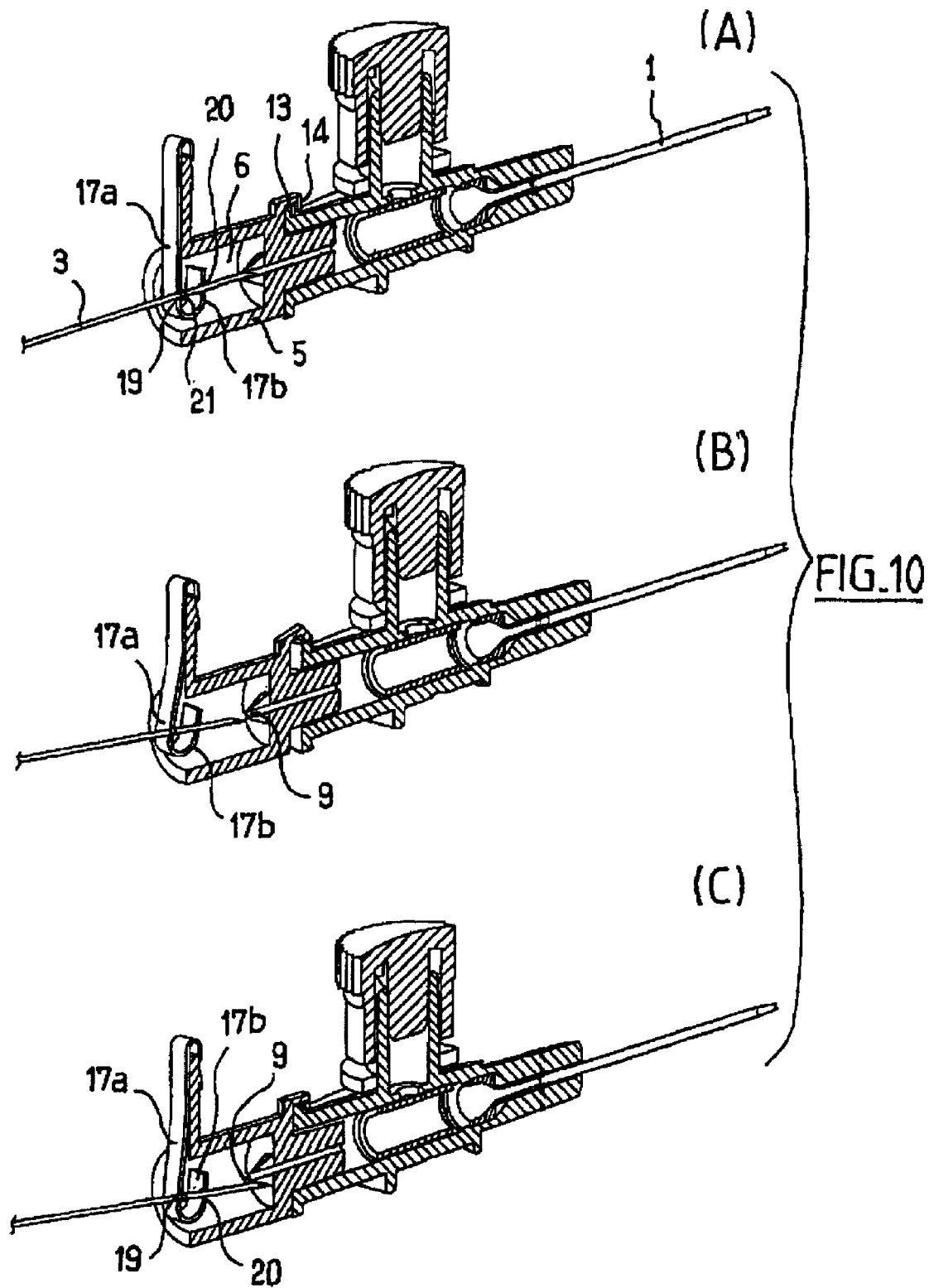
FIG. 10A is a view in perspective of an assembly according to FIG. 9, in which the base of the needle has been omitted, in which the assembly has been cut in two by a longitudinal plane of symmetry, and in which the needle has been withdrawn until the point of the needle is on the point of emerging into the chamber of the cage.
FIG. 10B is similar to FIG. 10A, during a later withdrawal stage, the point of the needle having arrived in the chamber of the cage, and the needle causing a deflection of the flexible blade.
FIG. 10C is similar to FIG. 10B, during a later stage in which the flexible blade has been pushed back by the needle until the point of the needle comes up against the front wall of the chamber of the cage.

By continuing the rearward traction on the needle, the blade is bent elastically and the bevelled end of the needle enters into the chamber. The deformation of the blade causes its hole to move off axis and as a consequence moves the needle off axis, this inclining within the chamber. By continuing the rearward traction, the cage is finally detached from the catheter base (FIG. 3).

The flexible blade then returns to its rest position and pushes the needle back by means of the bulge. The diverted bevelled end enters into the groove created around the exit of the chamber, where it is immobilised.

In the variant of FIG. 5, by drawing the needle to the rear, the slot in the wall of the needle is brought to the level of the claws of the blade. The claws dig into the latter and ensure axial immobilisation of the needle. By continuing the withdrawal movement of the needle, the blade is deformed, the cage separates from the cannula, and the blade returns to its original position. Even if the bevelled end were to succeed in recentring itself in the hole, the bevelled end will be blocked in the cage. A user who wanted to re-engage the bevelled end in the distal exit of the chamber could not do so.

The implementation of FIG. 9 is used like the preceding implementations, and has the advantage of even greater safety due to the fact that the needle is guided by the two perforations in the flexible U-shaped blade, which combine to constrain it to incline when the blade is bent.

In the implementation of FIG. 13, the traction on the needle, blocked fully back in the chamber, leads to a rearward traction on the blade. When the puncture end of the needle is in the chamber, the retention dog is able to mount onto the collar of the base so as to escape to the rear, allowing the cage to separate from the base.

The invention is not limited to these examples of implementation.

The invention claimed is:

1. An arrangement for the insertion into the body, through the skin, of a catheter with a proximal base, where this arrangement includes a needle which has a puncture end and a cage, which extends the base in the proximal direction, where this cage forms a chamber through which the needle slides from a proximal entrance to an opposite distal exit and is equipped with a sprung flexible steel blade to hold the puncture end of the needle in the chamber when the needle is withdrawn from the cannula, wherein this blade comprises a transverse branch positioned across the chamber close to the proximal entrance of the chamber perpendicular to the needle and traversed by the needle, where the blade and the needle include resources that combine so that the transverse branch is at rest and traversed freely by the needle when the needle is pushed in the distal direction, and so that the transverse branch stops the needle and is bent by the needle when the needle is drawn in the proximal direction beyond a given axial position, so that the bent transverse branch inclines the needle and applies a return force to the needle which tends to force the needle back in the distal direction until the puncture end comes up against a wall of the chamber.

2. An arrangement according to claim 1 in which the transverse branch has a perforation for the passage of the needle, and ahead of the said perforation, the needle has its section modified locally so that this section is stopped by the perforation in the transverse branch during the withdrawal movement of the needle in the proximal direction, this modified section being located at a distance from the puncture end of the needle so that the contact of the modified section with the perforation in the transverse branch occurs after this end has arrived in the chamber during the operation for removal of the needle.

3. An arrangement according to claim 1, in which the chamber has an end wall in the distal direction which includes a groove into which the puncture end of the inclined needle enters.

4. An arrangement according to claim 1, in which the transverse branch constitutes a branch of a blade shaped as an L, and which has a longitudinal branch fixed to a longitudinal wall of the chamber, the transverse branch being equipped with a perforation for the passage of the needle.

5. An arrangement according to claim 1, in which the transverse branch is shaped as a U, constituting a first rear transverse branch located at the entrance of the chamber, and equipped with a perforation for the passage of the needle, and a second front transverse branch parallel to the first branch, located in the said chamber and equipped with a perforation for the passage of the needle, where the perforation of the rear branch is not sufficiently large to allow passage of the modified section of the needle, but the perforation of the front branch is able to allow this section to pass.

6. An arrangement according to claim 5, in which the catheter base has an external rim and the cage includes a mobile lever which has a stop dog locked to this rim in one position of the lever, and in which the second front branch of the transverse branch is continued by a third branch more or less at the bracket of the second front branch, and which operates the said lever to release the dog.

7. An arrangement according to claim 1, in which, ahead of the chamber, the cage includes a nose which slots into the catheter base and which is traversed longitudinally by an aperture for the passage of the needle.

8. An arrangement according to claim 1, in which the needle is equipped with a base, and in which the cage includes a transverse plate projecting laterally, against which presses one wall of the base of the needle when the needle is in its working position.

9. An arrangement according to claim 8, in which the said blade is suspended from the said plate of the cage.

10. An arrangement according to claim 1, in which the needle includes a base bearing against the flexible blade when the needle is in its working position.

* * * * *